United States Patent [19]

Hendricks et al.

[11] Patent Number: 5,166,418
[45] Date of Patent: Nov. 24, 1992

[54] METHOD FOR PRODUCING IBUPROFEN

[75] Inventors: Joel D. Hendricks, Virginia Beach, Va.; Graham N. Mott, Corpus Christi, Tex.

[73] Assignee: Hoechst Celanese Corporation, Somerville, N.J.

[21] Appl. No.: 803,744

[22] Filed: Dec. 4, 1991

Related U.S. Application Data

[63] Continuation of Ser. No. 533,630, Jun. 4, 1990, abandoned.

[51] Int. Cl.$^5$ .............................................. C07C 51/10
[52] U.S. Cl. ................................................... 562/406
[58] Field of Search ........................................ 562/406

[56] References Cited

FOREIGN PATENT DOCUMENTS

| 284310 | 9/1988 | European Pat. Off. ............ 562/406 |
| 56-35659 | 9/1978 | Japan . |
| 55-27147 | 2/1980 | Japan . |
| 59-95238 | 6/1984 | Japan . |
| 59-95239 | 6/1984 | Japan . |
| 62-242641 | 10/1987 | Japan . |
| 62-242642 | 10/1987 | Japan . |
| 62-263140 | 11/1987 | Japan . |

*Primary Examiner*—Michael L. Shippen
*Attorney, Agent, or Firm*—Donald R. Cassady; Marvin Turken

[57] ABSTRACT

A method is provided for the preparation of ibuprofen by carbonylating 1-(4'-isobutylphenyl)ethanol (IBPE) with carbon monoxide comprising initially a reaction mixture comprising IBPE, ibuprofen and a catalyst for the carbonylation with carbon monoxide under conditions to initiate the reaction, and continuing to feed carbon monoxide to the composition to produce the desired yield of ibuprofen. Preferably the catalyst comprises palladium and a monodentate phosphine ligand. The presence of ibuprofen in the feed composition when the reaction is initiated with CO makes it possible to obtain high selectivities to ibuprofen with substantially complete conversion of IBPE at much shorter reaction times than if no ibuprofen is present initially.

12 Claims, No Drawings

METHOD FOR PRODUCING IBUPROFEN

This application is a continuation of prior U.S. application Ser. No. 07/533,630, filed Jun. 4, 1991, now abandoned.

BACKGROUND OF THE INVENTION

1. Field of the Invention

This invention relates to an improved method for the production of 2-(4'-isobutylphenyl)propionic acid, more commonly known as ibuprofen.

2. Description of Related Art

The following information is disclosed in accordance with the terms of 37 CFR 1.56, 1.97 and 1.98.

Ibuprofen is a well-known nonsteroidal anti-inflammatory drug which has been converted from ethical, i.e., prescription, to over-the-counter status.

Japanese Kokai Patent No. SHO 55 [1980]-27,147, published Feb. 27, 1980 and assigned to Mitsubishi Petrochemical Co., discloses the formation of aryl substituted carboxylic acids, e.g., α-(4'-isobutylphenyl)propionic acid or ibuprofen, by reacting an aryl-substituted alcohol, e.g., 1-(4-isobutylphenyl)ethanol, with carbon monoxide and water in the presence of a hydrogen fluoride catalyst.

Japanese Kokai Patent No. SHO 59 [1984]-95,238, published Jun. 1, 1984 and assigned to Mitsubishi Petrochemical Co., teaches the formation of phenylacetic acid derivatives such as α-aryl-substituted propionic acids, where the aryl group may be a phenyl group containing at least one alkoxy, aryloxy, hydroxy, or amino group as an electron-donor substituent, by reacting a benzyl alcohol derivative, which may be an α-aryl substituted ethanol wherein the aryl group is the same as in the phenylacetic acid derivative product, with carbon monoxide and water, alcohol, or phenol, in the presence of a palladium catalyst. An acidic compound such as hydrogen chloride may be added as an auxiliary catalyst and a solvent such as benzene may also be used. The disclosure includes a comparative example in which ibuprofen (not included within the invention) is obtained in very low yield, i.e., 17.1%, when made utilizing the described process.

Japanese Kokai Patent No. SHO 59 [1984]-95,239, published Jun. 1, 1984 and assigned to Mitsubishi Petrochemical Co., discloses the formation of α-(6-methoxy-2-naphthyl)propionic acid by reacting α-(6-methoxy-2-naphthyl)ethyl alcohol with carbon monoxide and water in the presence of a palladium catalyst and an acidic compound, e.g., hydrogen chloride. The patent publication also states that if a non-halogen-containing acidic compound is used, it is desirable to add an ionizable metal halide to the reaction.

Japanese Kokuku Patent No. SHO 56 [1981]-35,659, published Sep. 4, 1978 and assigned to Ferrel International Societe Annonim, discloses an anhydrous method of producing a 2-(4'-isobutylphenyl)propionic acid ester by treating 1-(4'-isobutylphenyl)ethanol (IBPE) with carbon monoxide in a solution containing an alkanol and a catalyst such as palladium bis(triphenylphosphine) dichloro complex. The solution may also contain up to 10% of a mineral acid such as hydrogen chloride.

Pending application Ser. No. 07/357,381, filed May 24, 1989 by V. Elango et al., discloses a method for the preparation of ibuprofen by carbonylating 1-(4'-isobutylphenyl)ethanol (IBPE) with carbon monoxide under certain specific conditions utilizing a palladium catalyst in an aqueous acid medium. The entire disclosure of this application is hereby incorporated by reference.

SUMMARY OF THE INVENTION

In accordance with this invention, 2-(4'-isobutylphenyl)propionic acid, i.e. ibuprofen, is prepared by the carbonylation of 1-(4'-isobutylphenyl)ethanol (IBPE) using a method comprising initially contacting carbon monoxide with a reaction mixture containing IBPE, ibuprofen and a catalyst for the carbonylation under conditions to initiate the reaction, and continuing to feed carbon monoxide to the composition to produce the desired amount of ibuprofen.

It has been found that the method of this invention, including the presence of ibuprofen in the initial feed composition, has a significant effect in reducing the amount of reaction time necessary to obtain a major proportion of the possible yield of ibuprofen.

DESCRIPTION OF PREFERRED EMBODIMENTS

The method of the invention is capable of yielding an advantage in reaction time using operable carbonylation catalyst and reaction conditions in an aqueous medium. This improvement in reaction time makes possible the use of continuous reaction processes in addition to the batch processes previously developed. Preferably, the reaction is carried out in an acidic aqueous medium using a catalyst comprising palladium and a monodentate phosphine ligand, and in the case of a batch reaction, or a continuous plug flow reaction, the operable conditions used are typically those disclosed in previously cited application Ser. No. 07/357,381. These conditions include carrying out a batch-type reaction in an acidic aqueous medium at a temperature of at least about 10° C. and a carbon monoxide pressure of at least about 500 psig, and in the presence of 1) a catalyst consisting essentially of a palladium compound in which the palladium has a valence of zero to 2 and is complexed with at least one acid stable, monodentate phosphine ligand freely miscible with the organic phase of the reaction medium, the phosphorus/palladium mole ratio in said palladium compound and ligand being at least about 2:1 when the mole ratio of palladium to IBPE is such that palladium=1 and IBPE=10,000 or more; 2) ionizable or dissociatable hydrogen ions in the form of an acid which is substantially ionizable in a dilute aqueous solution, e.g., of 0.1 N concentration, such that the mole ratio of hydrogen ions to IBPE added to the reaction zone (H+/IBPE) is at least about 0.15; and 3) ionizable or dissociatable halide ions such that the mole ratio of halide ions to IBPE added to the reaction zone (X−/IBPE) is at least about 0.15.

When the mole ratio of palladium to IBPE in the above-described reaction is such that palladium=1 and IBPE is less than 10,000, the phosphorous to palladium mole ratio in said palladium compound and ligand typically ranges from about 0.1 to about 50, although the maximum mole ratio of phosphorous to palladium does not appear to be critical.

The term "monodentate" is intended to mean a single phosphine phosphorus atom present in the ligand molecule before it is complexed with palladium. The phrase "freely miscible with the organic phase of the reaction medium" means that the ligand is not complexed with an insoluble substrate such as a polymer which prevents it from being freely mixed in the organic phase.

In carrying out a batch or continuous plug flow carbonylation reaction, the mole ratio of ibuprofen to IBPE at the initiation of the reaction, i.e., when the reaction composition is initially contacted with carbon monoxide under reaction conditions, may be in the range of about 0.01 to 2, preferably about 0.1 to 1.25; water may be present in an amount, for example, of about 10 to 600%, preferably about 15 to 100%, based on the weight of IBPE initially present; the temperature of reaction may be, for example, in the range of about 10° to 225° C., preferably about 70° to 175° C.; the carbon monoxide pressure may be, for example, in the range of about 500 to 5000 psig, preferably about 700 to 3000 psig; and the total reaction time may be, for example, in the range of about 0.25 to 2.0 hours, preferably about 0.25 to 0.75 hour. This compares with typical total reaction time periods of 2 hours to 2.5 hours to obtain an equivalent product yield when ibuprofen is not present at the initiation of the reaction.

In carrying out a continuous carbonylation reaction where backmixing occurs, the required mole ratio of ibuprofen to IBPE in the feed to the reaction system is expected to be higher, for example, in the range of about 15 to 1,000. This mole ratio requirement is affected by the concentration of reactants in the reaction system and by the concentration of ibuprofen required in the product exiting the reaction system. The preferred mole ratio of ibuprofen to IBPE in the feed to a continuous carbonylation reaction wherein substantial backmixing occurs is expected to range from about 20 to 200.

Some palladium catalysts which may be used wherein the palladium is complexed with an appropriate ligand are as follows: bis(triphenylphosphine) dichloro complex, bis(tributylphosphine) dichloro complex, bis(tricyclohexylphosphine) dichloro complex, pi-allyltriphenylphosphine dichloro complex, triphenylphosphine piperidine dichloro complex, bis(triphenylphosphine) dicarbonyl complex, bis(triphenylphosphine) diacetate complex, bis(triphenylphosphine) dinitrate complex, bis(triphenylphosphine) sulfate complex, tetrakis(triphenylphosphine) complex, and complexes in which some of the ligands are carbon monoxide such as chlorocarbonyl bis(triphenylphosphine) complex, all complexes of palladium. Also suitable as a catalyst is palladium metal on a suitable catalyst support such as carbon, alumina, silica, or an inert polymer which can tolerate the conditions of reaction, complexed with one or more of these foregoing ligands.

The palladium salts and phosphine ligands making up the foregoing catalyst complexes may also be added separately to the reaction zone. In this case, the amount of ligand added is preferably sufficient to complex with the palladium present such that the P:Pd mole ratio is equal to at least about 1:1 when the Pd:IBPE mole ratio is at least about 1:5,000. However, when the latter ratio is below about 1:10,000, it is necessary to use an excess of phosphine ligand such that the P:Pd ratio is at least about 2:1.

The catalyst complex may be present in an amount such that the mole ratio of palladium to IBPE is in the range, for example, of about 1:25 to 1:60,000, preferably about 1:150 to 1:50,000.

The ionizable or dissociatable hydrogen ions and halide ions may be conveniently added to the reaction as hydrogen chloride, hydrogen bromide, or hydrogen iodide. However, it is also possible to add the hydrogen ions and halide ions from separate sources. For example, other acids completely ionizable in dilute aqueous solution, e.g., inorganic acids, such as sulfuric acid, phosphoric acid or polyphosphoric acid, or organic acids, e.g., sulfonic acids such as p-toluenesulfonic acid, methanesulfonic acid, or trifluoroacetic acid, may be used as the source of hydrogen ions. Similarly, other water-soluble and ionizable halide compounds, as for example, halide salts wherein the cation does not interfere with the reaction, e.g., alkali metal halides such as potassium, sodium, and lithium chlorides, bromides, and iodides may be used as the source of halide ions. The mole ratio of hydrogen ions and halide ions to IBPE ($H^+$/IBPE and $X^-$/IBPE) each may be in the range, for example, of about 0.15 to 5, preferably about 0.3 to 2.0.

Although not necessary for the operability of the process, in some instances, it may be advantageous to utilize an organic solvent for the reaction. Organic solvents which can be used are, for example, ketones such as methyl ethyl ketone, acetone, 2-pentanone, 3-pentanone, and acetophenone, aromatic hydrocarbons such as benzene and toluene, and cyclic ethers such as tetrahydrofuran and dioxane. Ketones and ethers are preferred if a solvent is used. If the catalytic palladium as added to the system is in the metallic or zero valence state ($Pd^\circ$), then any solvent used should be non-hydrocarbon. The solvent may be present in a weight ratio of solvent to IBPE in the range, for example, of about 0 to 1000:1, preferably about 0 to 10:1.

An inorganic salt may also be present during the reaction. Inorganic salts which may be used are, for example, those yielding anions comprising oxygen, and sulfur, phosphorus, aluminum, or silicon, including such anions as hydrogensulfate, pyrosulfate, ortho-phosphate, pyrophosphate, aluminate, or silicate and cations such as sodium, potassium, calcium, or magnesium, or another cation which does not interfere with the reaction, e.g., ammonium or alkylammonium such as tetrabutylammonium. Other inorganic salts such as calcium chloride may also be added. The inorganic salt, if used, will generally be present at a concentration of, for example, about 0.1 to 50%, preferably about 1 to 20% by weight of total charge.

In some instances, an undesirable heavy ends fraction may form during the reaction, possibly due to a polymerization mechanism of unknown nature. In view of this, it may be beneficial to incorporate a polymerization inhibitor in the reaction mass. Inhibitors which may be used for this purpose include, for example, t-butylcatechol, hydroquinone, m-dinitrobenzene, N-nitrosodiphenylamine, picric acid, sodium sulfite, quinhydrone and the like. If an inhibitor is utilized, it may be incorporated in an amount, for example, of about 0.01 to 15%, preferably about 0.1 to 5% by weight based on the weight of IBPE.

As stated, the inventive method makes it possible to obtain a major proportion of the desired yield of ibuprofen in substantially less time than is the case when the initial reaction mixture containing IBPE does not also contain ibuprofen. This result can be exploited whether the method is carried out batchwise, semi-continuously or continuously. In batch operation, the ibuprofen is added to the reaction with the other components of the reaction mixture before the reaction is initiated with CO at the reaction temperature. After the conclusion of the reaction which requires a much shorter time (the reaction time can be, typically, one quarter of the reaction time required when no ibuprofen is added initially), the CO flow is cut off, the contents of the reactor are removed for purification, and the procedure is repeated with the next batch. In semicontinuous operation, the initial procedure is similar to batch operation. However, after the reaction is substantially concluded and the CO flow is cut off and the reaction vented, not all the contents of the reactor are removed for purification. Rather, a small amount of these contents, which contain a large proportion of ibuprofen, may be allowed to remain in the reactor to serve as a "heel", under the invention. Fresh amounts of the other components of the reaction mixture may then be added, including IBPE aqueous acid, and catalyst, and the reaction again initiated by contacting the mixture with CO and reestablishing reaction temperature. This procedure may then be repeated as many times as convenient. In continuous operation, if little or no backmixing occurs in the reactor as in the case of certain tubular reactors, the advantages of the inventive method may be obtained by continuously feeding ibuprofen into the reactor with the other components of the charge composition. This may be accomplished by recycling a small proportion of the product stream to the charge end of the reactor. If substantial backmixing occurs in the continuous reactor, then an advantage of the inventive method in terms of an increase in the initial reaction rate may be obtained by adding ibuprofen to the reactor with the other components of the feed so that such ibuprofen is present when CO feed is initiated.

Examples 1 to 20 further illustrate the inventor. In these examples, the "time of reaction" is the actual time that it takes for the reaction to proceed to substantial completeness as indicated by CO uptake. Such time, which may be also termed as the "period of actual reaction," is measured from the onset of the reaction at about 130° C., when the CO uptake ascribed to the reaction becomes significant, to the point at which such CO uptake is at or close to zero. Such measured time is different from the "time of reaction" given in the examples of previously cited application Serial No. 07/357,381 and its predecessor applicants, which was a previously set time from the onset of the reaction at about 130° C. to the point at which the reactor contents were cooled below the necessary reaction temperature prior to removal for subsequent handling. Although the latter preset time is generally estimated to be approximately equal to the period of actual reaction measured by CO uptake as previously defined, it could be somewhat higher or lower than such period.

EXAMPLES 1 to 20

To a 4 liter Hastalloy B autoclave were added varying amounts of IBPE, 36% or 26% aqueous hydrochloric acid, palladium chloride, triphenyl phosphine, and ibuprofen. The autoclave was sealed, purged with $N_2$ and CO, and pressured with CO to a level sufficient to result in a targeted reaction pressure at a reaction temperature of 130° C. or 140° C. The reactor contents were then heated to the latter reaction temperature and CO was fed to the reactor to maintain the desired pressure as the CO was absorbed during the reaction. Substantial completion of the reaction was determined by monitoring the CO uptake. In each case, conversion of IBPE was at least 99%. The conditions of reaction including quantities of reaction components (wherein ibuprofen is indicated as "IBU"), mole ratio of hydrogen ions to IBPE ($H^+$/IBPE) mole ratio of ibuprofen to IBPE (IBU/IBPE), temperature, time of reaction (i.e., the period of actual reaction measured by CO uptake as defined previously), pressure, and results of the reaction in terms of ibuprofen selectivity (IBU Sel.), are shown in the following table.

TABLE

| Example | IBPE, mmol | HCl, %/mL | $H^+$/IBPE | $PdCl_2$, mmol | $PPh_3$, mmol | IBU, mmol | IBU/IBPE | Temp. °C. | Time, min. | Press., psig | IBU/Sel., % (2%) |
| --- | --- | --- | --- | --- | --- | --- | --- | --- | --- | --- | --- |
| 1  | 5899 | 26/541 | 0.75 | 2.0 | 5.0 | 1969 | 0.33 | 130 | 90    | 1000 | 81 |
| 2  | 8427 | 26/775 | 0.75 | 2.8 | 6.9 | 2809 | 0.33 | 130 | 80–90 | 1500 | 90 |
| 3  | 8427 | 26/775 | 0.75 | 2.8 | 6.9 | 2809 | 0.33 | 130 | 70    | 2400 | 91 |
| 4  | 8427 | 26/775 | 0.75 | 2.8 | 6.9 | 2809 | 0.33 | 130 | 100   | 1500 | 90 |
| 5  | 5899 | 36/371 | 0.75 | 2.0 | 5.0 | 1967 | 0.33 | 130 | 70    | 2400 | 81 |
| 6  | 5899 | 36/371 | 0.75 | 2.0 | 5.0 | 1967 | 0.33 | 130 | 50–60 | 2400 | 90 |
| 7  | 5899 | 36/621 | 1.26 | 2.0 | 5.0 | 1967 | 0.33 | 140 | 80    | 1000 | 78 |
| 8  | 5899 | 26/906 | 1.26 | 2.0 | 5.0 | 1967 | 0.33 | 140 | —     | 2400 | 83 |
| 9  | 5899 | 26/541 | 0.75 | 2.0 | 5.0 | 3933 | 0.67 | 130 | 80    | 1500 | 85 |
| 10 | 8427 | 26/775 | 0.75 | 2.8 | 6.9 | 5618 | 0.67 | 130 | 90    | 2400 | 88 |
| 11 | 5899 | 26/541 | 0.75 | 2.0 | 5.0 | 5900 | 1.00 | 140 | 90    | 1000 | 82 |
| 12 | 5899 | 36/371 | 0.75 | 2.0 | 5.0 | 5900 | 1.00 | 140 | 30–40 | 2400 | 88 |
| 13 | 5899 | 36/371 | 0.75 | 2.0 | 5.0 | 5900 | 1.00 | 140 | 40–50 | 2400 | 94 |
| 14 | 5618 | 26/769 | 1.11 | 2.0 | 5.0 | 5632 | 1.00 | 130 | 50–60 | 2400 | 90 |
| 15 | 5618 | 26/775 | 1.13 | 2.8 | 6.9 | 5632 | 1.00 | 130 | 40    | 2400 | 85 |
| 16 | 5899 | 36/621 | 1.26 | 2.0 | 5.0 | 5900 | 1.00 | 130 | 80–90 | 1000 | 75 |
| 17 | 5899 | 36/621 | 1.26 | 2.0 | 5.0 | 5900 | 1.00 | 130 | 60    | 1000 | 54 |
| 18 | 5899 | 36/621 | 1.26 | 2.0 | 5.0 | 5900 | 1.00 | 130 | 100   | 1000 | 80 |
| 19 | 5899 | 26/906 | 1.26 | 2.0 | 5.0 | 5900 | 1.00 | 130 | 40–50 | 2400 | 83 |
| 20 | 5899 | 26/907 | 1.26 | 2.0 | 5.0 | 5900 | 1.00 | 130 | 30–40 | 2400 | 92 |

COMPARATIVE EXAMPLE A

The procedure of Example 3 was followed utilizing 26% HCl except that no ibuprofen was added with the initial feed components. The period of actual reaction as determined by CO uptake was about 120 minutes, the IBPE conversion was over 99% and the selectivity to ibuprofen ranged from about 93 to 95%.

COMPARATIVE EXAMPLE B

The procedure of Example 6 was followed utilizing 36% HCl, except that no ibuprofen was added with the initial feed components. The period of actual reaction as determined by CO uptake was about 130 minutes, the IBPE conversion was over 99% and the selectivity to ibuprofen ranged from about 93 to 95%.

A comparison of the results of Examples 3 and 6 with those of Comparative Examples A and B, respectively, indicate that the presence of ibuprofen in the feed composition when the reaction is initiated with CO make it possible to obtain high selectivities of ibuprofen with substantially complete conversion of IBPE at much shorter reaction times than if no ibuprofen is present.

We claim:

1. A method for production of ibuprofen by the carbonylation of 1-(4'-isobutylphenyl)ethanol (IBPE), wherein a reaction composition comprising said IBPE is contacted in a acidia aqueous medium with carbon monoxide in the presence of a catalyst for said carbonylation, under conditions to obtain said carbonylation reaction, wherein the improvement comprises:

having ibuprofen present in the initial reaction composition at the time said initial reaction composition is contacted with said carbon monoxide under reaction-obtaining conditions, and continually feeding carbon monoxide to said reaction composition as the reaction progresses, to produce the desired yield of ibuprofen.

2. The method of claim 1 wherein the reaction is a batch reaction or a continuous plug flow reaction and the mole ratio of ibuprofen to IBPE in said initial reaction composition is in the range of about 0.01 to 2.

3. The method of claim 1 wherein the reaction is a continuous reaction having a substantial amount of backmixing, and wherein the mole ratio of ibuprofen to IBPE at the initiation of the reaction with carbon monoxide is in the range of about 15 to 1,000.

4. The method of claim 3 wherein the mole ratio of ibuprofen to IBPE ranges from about 20 to 200.

5. The method of claim 1, claim 2 or claim 3 wherein said catalyst comprises palladium and a monodentate phosphine ligand.

6. The method of claim 2 wherein said carbonylation is carried out at a temperature of at least about 10° C. and a carbon monoxide pressure of at least about 500 psig, and in the presence of (1) a catalyst consisting essentially of a palladium compound in which the palladium has a valence of zero to 2 and is complexed with at least one acid stable, monodentate phosphine ligand miscible with the organic phase of the reaction medium, the phosphorus/palladium mole ratio in said palladium compound and ligand being at least about 2:1 when the mole ratio of palladium to IBPE is such that palladium $=1$ and IBPE$=10,000$ or more; (2) ionizable or dissociatable hydrogen ions in the form of an acid which is substantially ionizable in a dilute aqueous solution such that the mole ratio of hydrogen ions to IBPE added to the reaction zone is at least about 0.15; and (3) ionizable or dissociatable halide ions such that the mole ratio of halide ions to IBPE added to the reaction zone is at least about 0.15.

7. The method of claim 2 wherein the mole ratio of ibuprofen to IBPE at the initiation of the reaction with carbon monoxide is in the range of about 0.1 to 1.25.

8. The method of claim 6 wherein said palladium is added in the form of palladium chloride.

9. The method of claim 5 wherein said ligand is a tri(organo) phosphine.

10. The method of claim 9 wherein said ligand is triphenyl phosphine.

11. The method of claim 6 wherein the source of said hydrogen ions and halide ions is a hydrogen halide.

12. The method of claim 11 wherein said hydrogen halide is hydrogen chloride.

* * * * *